(12) United States Patent
Cook et al.

(10) Patent No.: US 7,276,621 B2
(45) Date of Patent: Oct. 2, 2007

(54) PRODUCTION OF DI-(2-ETHYLHEXYL) TEREPHTHALATE

(75) Inventors: Steven Leroy Cook, Kingsport, TN (US); Christopher Fletcher Tomlin, Kingsport, TN (US); Phillip Wayne Turner, Blountville, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/202,975

(22) Filed: Aug. 12, 2005

(65) Prior Publication Data

US 2007/0038001 A1 Feb. 15, 2007

(51) Int. Cl.
C07C 67/08 (2006.01)
(52) U.S. Cl. ...................................................... 560/99
(58) Field of Classification Search .................. 560/99
See application file for complete search history.

(56) References Cited

U.S. PATENT DOCUMENTS

| | | | |
|---|---|---|---|
| 5,326,864 A | 7/1994 | Besemer et al. | |
| 5,391,770 A | 2/1995 | Le Fur et al. | |
| 5,502,240 A * | 3/1996 | Pugach et al. | 560/99 |
| 5,532,495 A | 7/1996 | Bloomquist et al. | |
| 6,310,235 B1 * | 10/2001 | Gick | 560/99 |
| 2002/0028963 A1 | 3/2002 | Gubisch et al. | |

FOREIGN PATENT DOCUMENTS

| | | |
|---|---|---|
| JP | 60004151 | 1/1985 |
| JP | 60004151 A * | 1/1985 |
| JP | 60 004151 | 7/1985 |
| JP | 2001031794 | 2/2001 |
| JP | 2005 120019 A2 | 5/2005 |
| JP | 2005 306759 A2 | 11/2005 |
| RU | 2 114 100 C1 | 6/1998 |

OTHER PUBLICATIONS

Zeng, Chongyu; "Study of esterification rule in DOTP preparation"; XP0024138167 retrieved from STN Database accession No. 1995:468078; Chemical Abstracts Service, Columbus, Ohio.

Jiang, Pinping; "Synthesis of DOTP plasticizer by esterification"; XP002413816 retrieved from STN Database accession No. 1995:454573; Chemical Abstracts Service, Columbus, Ohio.

Notification of Transmittal of the International Search Report and the Written Opinion of the International Searching Authority, or the Declaration date of mailing Feb. 16, 2007 on the corresponding PCT application.

Meiqi, Fu; "A Technique of Producing Dioctyl Terephthalate and an Improvement in the Technique"; Tianjin Chemical Industry, China, vol. 20, No. 17, 2006.

* cited by examiner

*Primary Examiner*—Samuel A Barts
*Assistant Examiner*—Lalitha Nagubandi
(74) *Attorney, Agent, or Firm*—Brett L Nelson; Bernard J. Graves, Jr.

(57) ABSTRACT

Disclosed is a process for the preparation of di-(2-ethylhexyl) terephthalate by the esterification of terephthalic acid with 2-ethylhexanol at elevated temperature and pressure while the water of reaction is removed from the reaction mixture.

5 Claims, No Drawings

PRODUCTION OF DI-(2-ETHYLHEXYL) TEREPHTHALATE

FIELD OF THE INVENTION

This invention pertains to the preparation of di-(2-ethylhexyl) terephthalate from terephthalic acid (TPA). More specifically, this invention pertains to a process for the preparation of di-(2-ethylhexyl) terephthalate by the esterification of TPA with 2-ethylhexanol (EH) at elevated temperature and pressure while removing the water of reaction from the reaction mixture.

BACKGROUND OF THE INVENTION

Di-(2-ethylhexyl) terephthalate, also known as dioctyl terephthalate or DOTP, is used as a plasticizer in a variety of polymeric materials such as polyvinyl chloride. DOTP can be prepared by the titanate-catalyzed transesterification of dimethyl terephthalate (DMT) with EH. Direct esterifications of TPA with EH under conditions similar to those used for the transesterification of DMT have produced slow reaction rates and sporadic problems with foaming. US-2002028963-A1 discloses an esterification process wherein water is removed by azeotropic distillation together with an alcohol. JP-60004151-A (JP-03004052-B) discloses the reaction of TPA and EH under elevated pressures and temperatures. JP-2001031794-A discloses the preparation of terephthalic acid esters by reacting at least one of C9-C18 monohydric alcohol and 2-ethylhexanol with terephthalic acid. Water formed during the reaction was removed and the alcohol was separated and recirculated to the system. Finally, U.S. Pat. No. 5,532,495 discloses a multi-step esterification process that includes removing water and a portion of the alcohol reactant from the reaction mixture.

BRIEF SUMMARY OF THE INVENTION

We have developed a process for the preparation of di-(2-ethylhexyl) terephthalate by the esterification of TPA with EH at elevated pressure and temperature wherein the water of reaction and some of the EH is removed during the esterification process. The present invention therefore provides a process for the preparation of di-(2-ethylhexyl) terephthalate which comprises contacting TPA with EH in the presence of a titanium catalyst in a reaction zone wherein the total pressure is maintained at about 1 to 4 bar gauge, the temperature is maintained at about 180° to 270° C., the EH:TPA mole ratio is maintained at about 2:1 to 2.5:1, and an inert gas is passed through the TPA/EH reaction mixture in the reaction zone to cause a mixture of water and EH to be removed from the reaction zone during the preparation of di-(2-ethylhexyl) terephthalate. Our novel process provides the desired diester product at good reaction rates with high conversions of the TPA reactant with no observable foaming problems.

DETAILED DESCRIPTION

The esterification process of the present invention is carried out in a reaction zone comprising a pressure vessel while maintaining the EH:TPA mole ratio at about 2:1 to 2.5:1 The pressure and temperature within the reaction zone are maintained at about 1 to 4 bar gauge (barg) and about 180 to 270° C. Preferred pressure and temperature ranges are about 2 to 3.5 barg and about 180 to 260° C.

An important feature of the present invention is the removal of water of reaction along with EH during the esterification process. The maintenance of the EH:TPA mole ratio at about 2:1 to 2.5:1 requires the addition of EH to the reaction vessel during the process. The EH/water mixture or azeotrope removed from the reaction zone may be allowed to separate into an EH-rich organic phase and an aqueous phase and the EH-rich organic phase can be returned to the reaction zone. Alternatively, the EH:TPA mole ratio may be maintained at about 2:1 to 2.5:1 by the addition of fresh EH.

The removal of water of reaction from the reaction zone is assisted by passing an inert gas through the TPA/EH reaction mixture in the reaction zone. Nitrogen is the least expensive and thus is the preferred inert gas. The inert gas typically is fed below the surface of the TPA/EH reaction mixture by means of a conventional conduit or via a gas sparging device. While the inert gas may be fed intermittently or discontinuously, it preferably is fed continuously at the commencement of the esterification reaction. The amount of gas passed through the TPA/EH reaction mixture may vary significantly but typically is in the range of about 2 to 5 volumes of gas per volume of reaction mixture per hour.

The titanium catalyst may be any titanium compound soluble in the reaction mixture, i.e., soluble in EH and the di-(2-ethylhexyl) terephthalate product. An example of suitable titanium compounds include titanium tetraalkoxides having the formula $Ti(OR)_4$ wherein R is an alkyl group of 1 to 8 carbon atoms. The catalytically-effective amount of the titanium compound generally is an amount which provides a titanium [Ti] concentration of about 50 to 200 parts per million by weight in the reaction mixture. The process of the present invention may be carried out in a batch, semi-continuous or continuous mode. In the batch mode, an agitated pressure vessel is charged with TPA, EH and catalyst, heated and pressurized and the esterification is carried out while passing an inert gas through the reaction mixture. An EH/water mixture is removed and EH is fed to the reaction vessel over the course of the process. At the conclusion of the process, the di-(2-ethylhexyl) terephthalate product is recovered from the vessel and purified according to conventional procedures. Continuous operation involves continuously or intermittently feeding TPA, EH and catalyst to and continuously or intermittently removing EH, water and product-containing reaction mixture from a pressure vessel maintained at a predetermined temperature, pressure and liquid level. The product-containing reaction mixture may be fed to one or more secondary reaction vessels wherein conversion of TPA and/or TPA half-ester to the diester product is completed.

In the simplest embodiment, the reaction vessel may be fitted with one inlet for EH reactant return and a control valve to remove volatiles in lieu of a fractionation column. The reactor is charged with terephthalic acid, excess 2-ethylhexanol, and a catalytic amount of a titanium catalyst such as titanium tetraisopropoxide (TIPT). Heating and stirring of the mixture results in both an increase in pressure and esterification of the TPA to DOTP and the release of volatiles including EH and water. The volatile components consist primarily of the water of reaction and unreacted EH. These components can be swept out of the reactor with the aid of an inert gas purge, condensed and the 2-ethylhexanol separated from the water and returned to the autoclave via a pump. The product of this reaction typically is refined by filtering out unreacted TPA for recycle. The crude product (filtrate) is then neutralized with 2.5 weight percent aqueous NaOH, washed with water and filtered. Excess 2-ethylhexanol is stripped off at reduced pressure and the residue is then steam stripped. The stripped product is treated with activated carbon for one hour then filtered through a filter aid to give the final product.

In a preferred embodiment, the process may be practiced in a continuous mode by adding the TPA to a suitable reaction vessel by means of a screw feeder and the EH/catalyst as a pump-fed mixture to a stirred, pressurized reaction vessel equipped with a reflux condenser/decanter combination such that the water of reaction can be removed and the unreacted EH returned to the reactor. The effluent from this reactor can be passed to a chain of one or more polishing reactors wherein the conversion to DOTP with removal of water is continued. The product of this reaction can be further processed and refined by steps that are compatible with those listed for the batch example.

EXAMPLES

The process provided by the present invention is further illustrated by the following examples wherein all percentages given are by weight unless specified otherwise.

A 500 milliliter autoclave was charged with 137.9 g (0.83 mole) TPA, 250 g (1.92 moles) EH and 125 ppm (0.048 g) TIPT catalyst. The autoclave was equipped with a stirrer, a conduit for feeding EH and nitrogen below the surface of the TPA/EH catalyst mixture, a pressure relief conduit and a conduit fitted with a control valve (backpressure regulator) for the removal of water and EH. The autoclave then was sealed and heated to approximately 180° C. to generate a pressure of 1 barg within the autoclave. As the reaction proceeded, a mixture of water and EH was removed and the EH was pumped back to the autoclave. Nitrogen was fed with the recycled EH to facilitate removal of water. Total reaction time was 10.5 hours at a maximum temperature of 260° C. and a maximum autoclave pressure of approximately 3 barg. Unreacted TPA (14 g) was recovered by filtration. The crude product then was neutralized with 2.5% aqueous NaOH, washed with water and filtered. Excess EH was stripped off at reduced pressure and the residue then steam stripped. The stripped product was treated with activated carbon at 90° C. for one hour then filtered through a filter aid to give 136.6 g of product (~80% conversion). Analysis (Gas Chromatography, area percentages): 0.04% EH; 0.07% di-(2-ethylhexyl) phthalate, 0.13% methyl (2-ethylhexyl) terephthalate; 0.02% unknown; 99.42% DOTP. Color (PCS): 20.

A comparative experiment was performed at atmospheric pressure. To a 2-liter, round-bottom flask equipped with overhead stirrer, thermometer, heating mantel and vapor decanter was added 350 g (2.107 mol) of TPA, 687 g (5.28 mol) of EH and 0.208 g (200 ppm) of TIPT. Upon heating, the reaction began at ~180° C. The temperature slowly reached 189° C. in 6 hours. A temperature of 202° C. was achieved after 10 hours reaction time. The temperature was held at about 205° C. until ~14 hours of reaction time were completed. The temperature then reached 210° C. at 15 hours, 222° C. at 18 hours and the final temperature was 230° C., where it was held for 2 hours. A reaction time of 21.5 hours was therefore required before water evolution slowed to the point that the reaction was discontinued. A total of 73.5 g of water-containing distillate was collected out of a theoretical amount of 75.8 g. The crude product was stripped of volatiles, giving a total of 125.3 g. The residue weighed 733.7 g for a yield of 88.9%. Analysis (Gas Chromatography, area percentages): 0.04% EH; 0.04% di-(2-ethylhexyl) phthalate, 0.36% DOTP Isomer; 99.39% DOTP. Color (PCS): 40.

The invention has been described in detail with particular reference to preferred embodiments thereof, but it will be understood that variations and modifications can be effected within the spirit and scope of the invention.

We claim:

1. Process for the preparation of di-(2-ethylhexyl) terephthalate which comprises contacting terephthalic acid (TPA) with 2-ethylhexanol (EH) in the presence of a titanium catalyst in a reaction zone wherein the total pressure is maintained at about 1 to 4 bar gauge (barg), the temperature is maintained at about 180° C. to 270° C., the EH:TPA mole ratio is maintained at about 2:1 to 2.5:1, and an inert gas is fed below the surface of the TPA/EH reaction mixture in the reaction zone, in the range of about 2 to 5 volumes of gas per volume of reaction mixture per hour, to cause a mixture of water and EH to be removed from the reaction zone during the preparation of di-(2-ethylhexyl) terephthalate.

2. Process according to claim 1 wherein the inert gas is passed through the TPA/EH reaction mixture at a rate of about 2 to 5 volumes of gas per volume of reaction mixture per hour.

3. Process according to claim 2 wherein the titanium catalyst is a titanium tetraalkoxide having the formula $Ti(OR)_4$ wherein R is an alkyl group of 1 to 8 carbon atoms.

4. Process for the preparation of di-(2-ethylhexyl) terephthalate which comprises contacting terephthalic acid (TPA) with 2-ethylhexanol (EH) in the presence of a titanium tetraalkoxide catalyst in a reaction zone wherein the total pressure is maintained at about 2 to 3.5 bar gauge (barg), the temperature is maintained at about 180° to 260° C., the EH:TPA mole ratio is maintained at about 2:1 to 2.5:1, and an inert gas is passed through the TPA/EH reaction mixture in the reaction zone at a rate of about 2 to 5 volumes of gas per volume of reaction mixture per hour to cause a mixture of water and EH to be removed from the reaction zone during the preparation of di-(2-ethylhexyl) terephthalate.

5. Process according to claim 4 wherein the titanium tetraalkoxide catalyst has the formula $Ti(OR)_4$ wherein R is an alkyl group of 1 to 8 carbon atoms and the concentration of the catalyst in the reaction mixture is an amounts which provides a titanium [Ti] concentration of about 50 to 200 parts per million by weight.

* * * * *